United States Patent
Jeong et al.

(10) Patent No.: US 9,731,269 B2
(45) Date of Patent: Aug. 15, 2017

(54) METHOD AND APPARATUS FOR SEPARATING CARBON AND OXYGEN ISOTOPES BY USING OPTICAL FIBER LASER

(75) Inventors: Do-Young Jeong, Daejeon (KR); Hyoun-Min Park, Daejeon (KR); Yong-Ho Cha, Daejeon (KR); Dong-Yong Chung, Daejeon (KR)

(73) Assignee: Korea Atomic Energy Research Institute, Daejeon (KR)

( * ) Notice: Subject to any disclaimer, the term of this patent is extended or adjusted under 35 U.S.C. 154(b) by 0 days.

(21) Appl. No.: 14/360,810

(22) PCT Filed: Jul. 19, 2012

(86) PCT No.: PCT/KR2012/005773
§ 371 (c)(1),
(2), (4) Date: May 27, 2014

(87) PCT Pub. No.: WO2013/077528
PCT Pub. Date: May 30, 2013

(65) Prior Publication Data
US 2014/0301938 A1      Oct. 9, 2014

(30) Foreign Application Priority Data

Nov. 25, 2011   (KR) .................. 10 2011 0124453

(51) Int. Cl.
*B01J 19/12*      (2006.01)
*B01D 59/34*      (2006.01)
(Continued)

(52) U.S. Cl.
CPC ............ *B01J 19/123* (2013.01); *B01D 59/34* (2013.01); *C01B 13/0237* (2013.01); *C01B 31/02* (2013.01); *C07C 45/78* (2013.01)

(58) Field of Classification Search
None
See application file for complete search history.

(56) References Cited

U.S. PATENT DOCUMENTS 3,983,020 A    9/1976  Moore et al.
4,029,558 A    6/1977  Marling
(Continued)

FOREIGN PATENT DOCUMENTS

CN    1756586 A    4/2006
CN    1939839 A    4/2007
(Continued)

OTHER PUBLICATIONS

Mannik, L and Brown, S.K., Appl. Phys. B 37, 79-86 (1985).*
(Continued)

*Primary Examiner* — Melvin C Mayes
*Assistant Examiner* — Sheng H Davis
(74) *Attorney, Agent, or Firm* — The Webb Law Firm (57) ABSTRACT

Provided is a method of separating carbon and oxygen isotopes by using a laser. In one preferred embodiment, the method includes performing a photolysis process on formaldehyde including a carbon or oxygen isotope by irradiation with ultraviolet light having a wavelength ranging from 340 nm to 360 nm to generate carbon monoxide having a carbon or oxygen isotope enriched therein and hydrogen, performing a catalytic reaction on the carbon monoxide having a carbon or oxygen isotope enriched therein and the hydrogen to synthesize carbon dioxide ($CO_2$) and water ($H_2O$) having a carbon or oxygen isotope enriched therein, and cooling the $H_2O$ to recover $CO_2$ having a carbon isotope enriched therein or $H_2O$ having an oxygen isotope enriched therein.

8 Claims, 5 Drawing Sheets

(51) Int. Cl.
*C01B 13/02* (2006.01)
*C01B 31/02* (2006.01)
*C07C 45/78* (2006.01)

(56) References Cited

U.S. PATENT DOCUMENTS

| | | | |
|---|---|---|---|
| 4,029,559 | A | 6/1977 | Marling |
| 4,212,717 | A * | 7/1980 | Moore et al. ............ 204/157.22 |
| 4,254,348 | A | 3/1981 | Stappaerts |
| 4,406,763 | A | 9/1983 | Hsu et al. |
| 4,941,956 | A | 7/1990 | Arai et al. |
| 5,085,748 | A | 2/1992 | Yamasaki et al. |
| 5,286,468 | A * | 2/1994 | Chang et al. ................. 423/249 |
| 5,314,592 | A | 5/1994 | Majima et al. |
| 5,859,070 | A * | 1/1999 | Jackson et al. ............... 518/713 |
| 6,113,869 | A * | 9/2000 | Jain ........................ B01D 53/04 423/219 |
| 6,321,565 | B1 | 11/2001 | Kihara et al. |
| 6,461,583 | B1 * | 10/2002 | Hayashida et al. ........... 423/579 |
| 6,653,587 | B1 | 11/2003 | Rizzo et al. |
| 7,346,084 | B1 | 3/2008 | Han |
| 7,493,447 | B2 | 2/2009 | Chuang |
| 2004/0089532 | A1 * | 5/2004 | Brooks et al. ............ 204/157.15 |
| 2005/0110485 | A1 * | 5/2005 | Sood .................. G01R 33/4831 324/307 |
| 2006/0249366 | A1 | 11/2006 | Hayashida |
| 2008/0108715 | A1 | 5/2008 | Haake et al. |
| 2008/0129994 | A1 * | 6/2008 | Murnick ............ G01N 21/1717 356/318 |
| 2009/0185583 | A1 * | 7/2009 | Kuksenkov et al. ............. 372/5 |
| 2010/0266477 | A1 * | 10/2010 | Ishii ........................ C10J 3/463 423/437.1 |
| 2010/0302626 | A1 * | 12/2010 | Kakui ............................ 359/334 |

FOREIGN PATENT DOCUMENTS

| | | |
|---|---|---|
| DE | 10 2005 001 290 A1 | 7/2006 |
| EP | 1 676 625 A1 | 12/2005 |
| JP | S54-012290 | 1/1979 |
| JP | 55-086524 | 6/1980 |
| JP | 09-192456 A | 7/1997 |

OTHER PUBLICATIONS

Yang, Fei, et al. "Oxidation of methanol and formaldehyde to CO2 by a phtocatalyst with an energy storage ability". Phys. Chem. Chem. Phys. 12, 5166-5170 (2010).*
Marling, Jack. "Isotope separation of oxygen-17, oxygen-18, carbon-13 and deuterium by ion laser induced formaldehyde photopredissocation". THe Journal of Chemical Physics. vol. 66, No. 9 May 1977.*
Hiraoka, Kenzo, et al. "Formation of Formaldehyde by the TUnneling Reaction of H with Solid Co at 10K revisted". The Astrophysical Journal, 577, 265-170, Sep. 20, 2002.*
Noguchi, Tetsuro, et al. "Photocatalytic Degradation of Gaseous Formaldehyde using TiO2 film". Environmental Science & Technology. 32, 3831-3833 (1998).*
Marling, John, "Isotope separation of oxygen-17, oxygen-18, carbon-13, and deuterium by ion laser induced formaldehyde photopredissociation", May 1, 1977, p. 4200-4225, vol. 66, No. 9, American Institute of Physics.
Laptev, V.B., et al., "Results and prospects of laser separation of oxygen isotopes by IR multiphoton dissociation of molecules", 1995, p. 607-614, vol. 22, No. 6, Kvantovaya Elektronika.
Hedges, R.E.M., et al., "Enrichment of Carbon-14 by Selective Laser Photolysis of Formaldehyde", 1980, p. 25-32, vol. 23, Applied Physics.
Yeung, Edward S., et al., "Isotopic separation by photopredissociation", Aug. 1, 1972, p. 109-110, vol. 21, No. 3, Applied Physics Letters.
Laptev, V.B., et al., "Laser Separation of Oxygen Isotopes by IR Multiphoton Dissociation of (CH3)2O", 1989, p. 77-83, vol. 49, Applied Physics B.
Mannik, L., et al., "Laser Enrichment of Carbon-14", 1985, p. 79-86, vol. 37, Applied Physics B.
Kawalczyk, "Highly Selective Molecular Laser Isotope Separation of Carbon-13", Laboratory of Physical Chemistry Molecular, Department of Chemistry, Federal Institute of Technology in Lausanne, 2000, No. 2276.

* cited by examiner

METHOD AND APPARATUS FOR SEPARATING CARBON AND OXYGEN ISOTOPES BY USING OPTICAL FIBER LASER

CROSS-REFERENCE TO RELATED APPLICATIONS

This application is the United States national phase of International Application No. PCT/KR2012/005773 filed Jul. 19, 2012, and claims priority to Korean Patent Application No. 10-2011-0124453 filed Nov. 25, 2011, the disclosures of which are hereby incorporated in their entirety by reference.

TECHNICAL FIELD

The present invention relates to a method of separating carbon and oxygen isotopes by using a laser, and more particularly, to a method and an apparatus for effectively separating and producing commercially useful carbon and oxygen isotopes by using an optical fiber laser having high energy efficiency and easy maintenance features.

BACKGROUND ART

In its natural state, carbon (C) has two types of stable isotopes, $^{12}C$ and $^{13}C$, having an abundance ratio of 98.85% and 1.11%, respectively. Also, oxygen (O) has three types of stable isotopes, $^{16}O$, $^{17}O$, and $^{18}O$ having an abundance ratio of 99.759%, 0.037%, and 0.204%, respectively. Among these carbon and oxygen isotopes, $^{13}C$, $^{17}O$ and $^{18}O$ isotopes are very useful commercially.

$^{13}C$ is used as a tracer having useful applications in chemistry, biochemistry, and environmental science, and labeled compounds, in which carbon atoms are substituted with $^{13}C$ isotopes in compounds such as urea, glucose, and fructose are usefully employed in medical studies and medical diagnoses of the human body. Accordingly, worldwide demand for $^{13}C$ is on the level of a few hundred kilograms per year and the market size thereof reaches tens of millions of dollars. Carbon having 99% or more of a $^{12}C$ isotope enriched therein is used for manufacturing diamond having improved thermal conductivity.

Meanwhile, positron emission tomography (PET), the use of which in the early diagnosis of cancer has been greatly increased, mostly uses fluorodeoxyglucose ($^{18}FDG$) as a diagnostic reagent, $^{18}FDG$ being an $^{18}F$ radioactive isotope-labeled compound. The $^{18}F$ radioactive isotope is produced by using $^{18}O$-enriched water having 96% or more of an $^{18}O$ isotope enriched therein as a raw material in a cyclotron accelerator. Worldwide demand for $^{18}O$-enriched water is on the level of a few tons per year, creating a market size of hundreds of millions of dollars, and annual market growth rate of 10% or more.

Also, materials used as coolants and as structural materials in a nuclear reactor may include $^{17}O$, $^{15}N$, and $^{13}C$. These stable isotopes react with reactor neutrons to generate $^{14}C$ radioactive isotopes. Since $^{14}C$, generated in a nuclear reactor, is very harmful in the case it leaks therefrom or from a radioactive waste disposal facility, the need to separate and safely store $^{14}C$ has become apparent. Currently, the amount of nuclear graphite waste stored in the world is about 300,000 tons and it is expected this amount will be greatly increased in the future. Therefore, a technique of reducing the amount of and safely managing nuclear waste through the separation and disposal of $^{14}C$ is very important.

Currently, the most common process used as a method of separating a carbon isotope is a method of separating a carbon isotope existing in liquid phase carbon monoxide through cryogenic distillation. This method uses a process in which a difference in vapor pressures of liquid phase $^{12}CO$ and $^{13}CO$ is about 1% at a pressure of about 1 atmosphere and at a temperature near 68K, a condensation temperature of carbon monoxide. U.S. Pat. No. 5,286,468 suggests a method of separating a $^{14}C$ radioactive isotope by the cryogenic distillation of carbon monoxide.

A most generalized method of separating an oxygen isotope is also a distillation method. When liquid oxygen is subjected to cryogenic distillation at a pressure of 1 atmosphere and at a temperature of 90K, an isotope enrichment factor of oxygen molecules, i.e., an enrichment factor ($\alpha$) of $^{16}O_2$ and $^{16}O^{18}O$, is about 1.012.

Also, a water distillation method is a method of separating an oxygen isotope by using a process in which vapor pressures are different according to isotopes constituting water ($H_2O$). That is, an enrichment factor ($\alpha$) of $H_2^{16}O_2$ and $H_2^{18}O$ at 320 K is about 1.007. U.S. Pat. Nos. 6,321,565 and 7,493,447 suggest a method of separating an oxygen isotope through a combination of cryogenic distillation and water distillation methods.

In an isotope separation facility using a distillation method, a degree of enrichment of a final product relates to a height of a distillation column and yield relates to a diameter thereof. With respect to the water distillation method, since the number of theoretical stages per meter (NTSM) of the best distillation packing is about 5, the height of the distillation column must be a minimum of 500 meters in order to enrich 0.2% of $^{18}O$ to 95% thereof.

With respect to U.S. Pat. Nos. 6,321,565 and 7,493,447, in which cryogenic distillation and water distillation are combined, the height of the distillation column is about 500 meters. Thus, a very large production facility may be required in order to separate carbon and oxygen isotopes by using a distillation method. Also, since a start-up time, a time before products are produced after starting an operation of the facility, may be relatively long, in a range of about 1 month to about 6 months, proper yield management may be difficult.

A method of separating carbon and oxygen isotopes by using a laser has advantages in that a size of a facility therefor may be relatively small and a start-up time may be very short. Methods of separating hydrogen, carbon, and oxygen isotopes through photolysis or photodissociation of formaldehyde by using an ultraviolet laser were devised in the late 1970' and the early 1980'. However, developments in overall processing were not completed and above all, the methods were not developed as viable commercial techniques as efficient ultraviolet lasers were not available.

Methods of separating carbon and oxygen isotopes by using a laser are described in U.S. Pat. Nos. 3,983,020, 4,029,558, 4,029,559, 4,212,717, and 4,254,348, and in articles contained in publications such as "Applied Physics, Vol. 23, 25 (1980)," "Applied Physics B, Vol. 37, 79 (1985)," "Applied Physics Letters, Vol. 21, 109 (1972)," and "The Journal of Chemical Physics, Vol. 66, 4200 (1977)."

Methods of separating a carbon or oxygen isotope by infrared multiphoton dissociation have also devised. These methods are described in U.S. Pat. Nos. 6,653,587, 5,314, 592, 5,085,748, 4,941,956, and 4,406,763, and articles in publications such as "Applied Physics B, Vol. 49, 77 (1989)" and "Quantum Electronics, Vol. 22, 607 (1995)."

These prior art documents suggest a method of separating carbon and oxygen isotopes through the multiphoton dissociation of $CF_3H$ or freon ($CHClF_2$) gas by using a highly energy-efficient carbon dioxide laser having an infrared light wavelength. However, this method has also not been developed as a commercial technique, as the maintenance and use of a gas laser may be difficult and extraction and recovery treatments of products may not be facilitated.

An aspect of the present invention provides a useful method of separating and producing carbon and oxygen isotopes by using an optical fiber laser having high energy efficiency and easy maintenance features in the photolysis of formaldehyde ($CH_2O$) for separating carbon and oxygen isotopes.

Another aspect of the present invention provides an optical fiber laser apparatus suitable for separating carbon and oxygen isotopes.

Another aspect of the present invention provides an effective method of enriching a carbon isotope which does not include radioactive carbon by removing a radioactive carbon isotope therefrom.

SUMMARY OF THE INVENTION

According to an aspect of the present invention, there is provided a method of separating a carbon isotope including: performing a photolysis process on formaldehyde, including a carbon isotope, by irradiation thereof with ultraviolet light having a wavelength ranging from 340 nm to 360 nm to generate carbon monoxide having a carbon isotope enriched therein and hydrogen; performing a catalytic oxidation reaction on the carbon monoxide having a carbon isotope enriched therein and the hydrogen to synthesize carbon dioxide ($CO_2$) having a carbon isotope enriched therein and water ($H_2O$); and cooling the $H_2O$ to recover $CO_2$ having a carbon isotope enriched therein.

The photolysis process may be performed by irradiation with a third harmonic generated by an optical fiber laser.

After infrared light having a wavelength ranging from 1020 nm to 1080 nm is pulse modulated and amplified by an optical fiber amplifier, the ultraviolet light having a wavelength ranging from 340 nm to 360 nm may be formed by converting the infrared light into a third harmonic.

After the performing of the photolysis process, the method may further include: performing formaldehyde synthesis for synthesizing formaldehyde having a carbon isotope enriched therein by using hydrogen and carbon monoxide having a carbon isotope enriched therein generated by the photolysis process; and performing a second photolysis process for generating carbon monoxide having a carbon isotope enriched therein and hydrogen through photolysis by irradiating the formaldehyde having a carbon isotope enriched therein with ultraviolet light having a wavelength range of 340 nm to 360 nm.

Methanol is synthesized from the hydrogen and the carbon monoxide having a carbon isotope enriched therein by a catalytic reaction, and the formaldehyde having a carbon isotope enriched therein may be synthesized from the synthesized methanol by a catalytic reaction.

According to another aspect of the present invention, there is provided a method of separating an oxygen isotope including: performing a photolysis process on formaldehyde including an oxygen isotope by irradiation with ultraviolet light having a wavelength ranging from 340 nm to 360 nm to generate carbon monoxide having an oxygen isotope enriched therein and hydrogen; performing a catalytic methanation reaction on the carbon monoxide having an oxygen isotope enriched therein and the hydrogen to synthesize water ($H_2O$) and methane ($CH_4$); and cooling the $H_2O$ to recover $H_2O$ having an oxygen isotope enriched therein.

The photolysis process may be performed by irradiation with a third harmonic generated by an optical fiber laser.

After infrared light having a wavelength ranging from 1020 nm to 1080 nm is pulse modulated and amplified by an optical fiber amplifier, the ultraviolet light having a wavelength ranging from 340 nm to 360 nm may be formed by converting the infrared light into a third harmonic.

After the performing of the photolysis process, the method may further include: performing formaldehyde generation for generating formaldehyde having an oxygen isotope enriched therein by using hydrogen and carbon monoxide having an oxygen isotope enriched therein generated by the photolysis process; and performing a second photolysis process for generating carbon monoxide having an oxygen isotope enriched therein and hydrogen through photolysis by irradiating the formaldehyde having an oxygen isotope enriched therein with ultraviolet light having a wavelength range of 340 nm to 360 nm.

Methane and water are synthesized from the hydrogen and the carbon monoxide having an oxygen isotope enriched therein by a catalytic methanation reaction, and the formaldehyde having an oxygen isotope enriched therein may be generated by mixing the synthesized water with formaldehyde to generate an oxygen-isotope exchange reaction between the water and the formaldehyde.

According to another aspect of the present invention, there is provided an optical fiber laser apparatus including: a main oscillator irradiating a laser having a wavelength range of 1020 nm to 1080 nm; an intensity modulator modulating a pulse of the laser; a plurality of ytterbium-doped fiber amplifiers amplifying a power of the pulse modulated laser; and second and third harmonic generators converting a wavelength of the power amplified laser into an ultraviolet light wavelength ranging from 340 nm to 360 nm.

According to another aspect of the present invention, there is provided a method of removing a $^{14}C$ radioactive carbon isotope including: performing a photolysis process on formaldehyde including a $^{14}C$ radioactive carbon isotope to photolyze into carbon monoxide (CO) including a $^{14}C$ radioactive carbon isotope and hydrogen ($H_2$) by irradiation with ultraviolet light having a wavelength range of 340 nm to 360 nm; and cooling and condensing formaldehyde remaining in the performing of the photolysis process to capture formaldehyde having the $^{14}C$ radioactive carbon isotope removed therefrom.

The photolysis process may be performed by irradiation with a third harmonic generated by an optical fiber laser.

After infrared light having a wavelength ranging from 1020 nm to 1080 nm is pulse modulated and amplified by an optical fiber amplifier, the ultraviolet light having a wavelength ranging from 340 nm to 360 nm may be formed by converting the infrared light into a third harmonic.

According to an embodiment of the present invention, an optical fiber laser having high energy efficiency and easy maintenance features is used in the photolysis process of formaldehyde and thus, it is commercially useful for separating carbon and oxygen isotopes as well as being economical, as carbon and oxygen isotopes may be separated and produced in a small-scale facility.

Also, according to an embodiment of the present invention, annual production of $^{18}O$-enriched water having 95% of $^{18}O$ and $^{13}C$-enriched carbon dioxide ($^{13}CO_2$) having 99% of $^{13}C$ may be innovatively increased and a facility start-up time may be decreased.

Further, disposal of nuclear carbon waste, such as nuclear graphite, may be effectively performed, as effective separation and removal of a $^{14}C$ radioactive isotope may be possible by using small-scale facility and apparatus.

Also, it may be suitable for a commercial application because maintenance and use of a gas laser may be simple and extraction and recovery treatments may be facilitated thereby.

BRIEF DESCRIPTION OF DRAWINGS

The above and other aspects, features and other advantages of the present invention will be more clearly understood from the following detailed description taken in conjunction with the accompanying drawings, in which.

DETAILED DESCRIPTION OF THE INVENTION AND BEST MODE FOR CARRYING OUT SAME

The present invention relates to a method and an apparatus for separating and producing commercially useful carbon and oxygen isotopes through a photolysis of formaldehyde by using an optical fiber laser.

When formaldehyde ($CH_2O$), composed of two hydrogen atoms, one carbon atom, and one oxygen atom is irradiated with light having a wavelength ranging from 340 nm to 360 nm, formaldehyde is photolyzed into a hydrogen molecule ($H_2$) and a carbon monoxide (CO). The present invention relates to a method of separating and recovering carbon and oxygen isotopes from formaldehyde through the irradiation of ultraviolet light having a specific wavelength by using an optical fiber laser.

Hereinafter, embodiments of the present invention will be described in detail with reference to the accompanying drawings.

Figure 1:
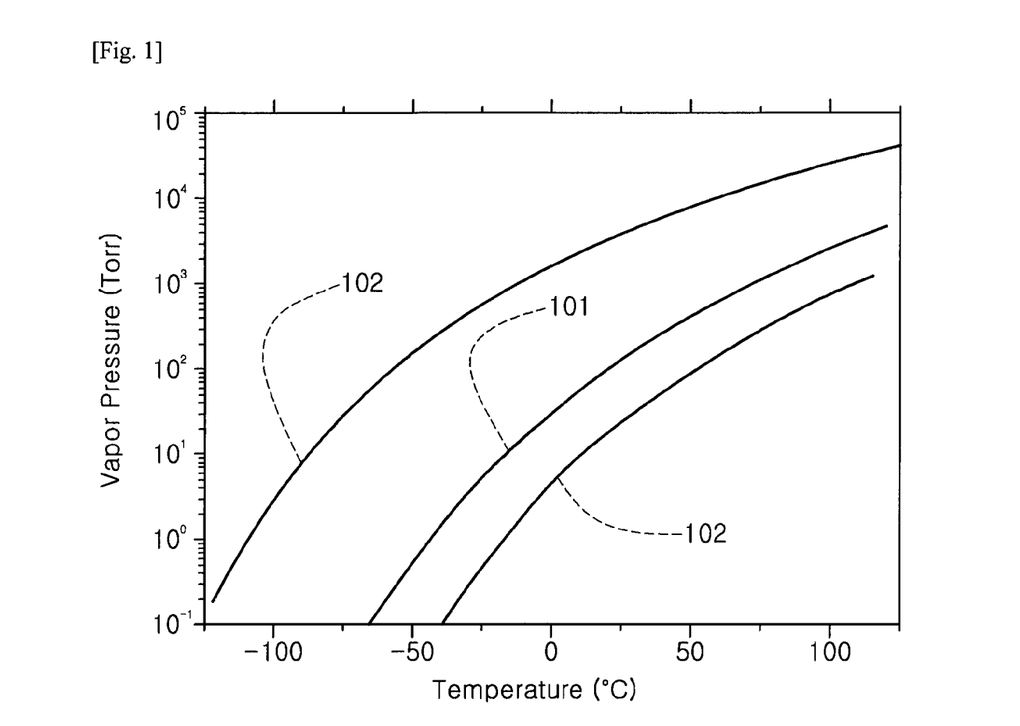
FIG. 1 is a graph showing vapor pressure curves of formaldehyde, methanol, and water according to a temperature, in which 100 represents a vapor pressure curve of formaldehyde according to a temperature, 101 represents a vapor pressure curve of methanol according to a temperature, and 102 represents a vapor pressure curve of water according to a temperature.
Figure 2:
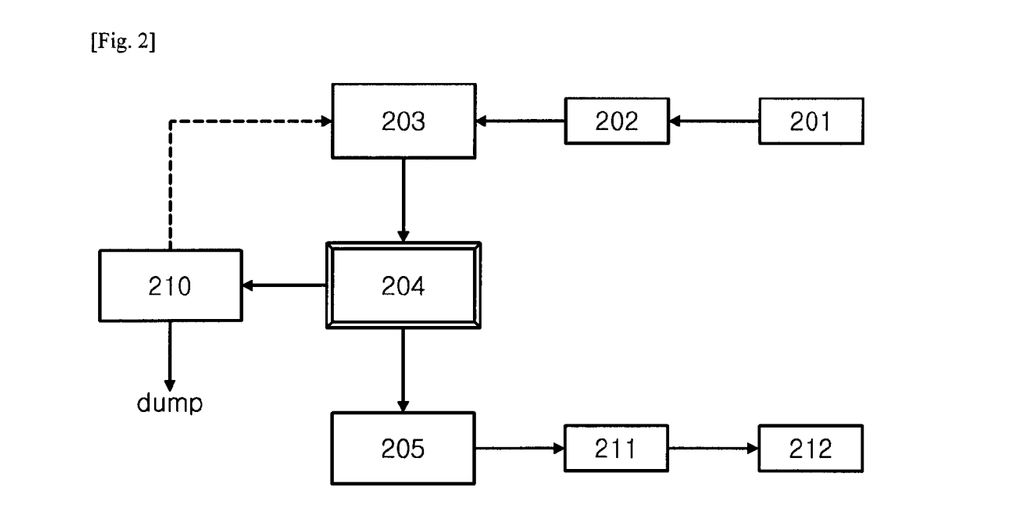
FIG. 2 is a block diagram schematically illustrating a separation process of a $^{13}C$ isotope according to an embodiment of the present invention.
Figure 3:
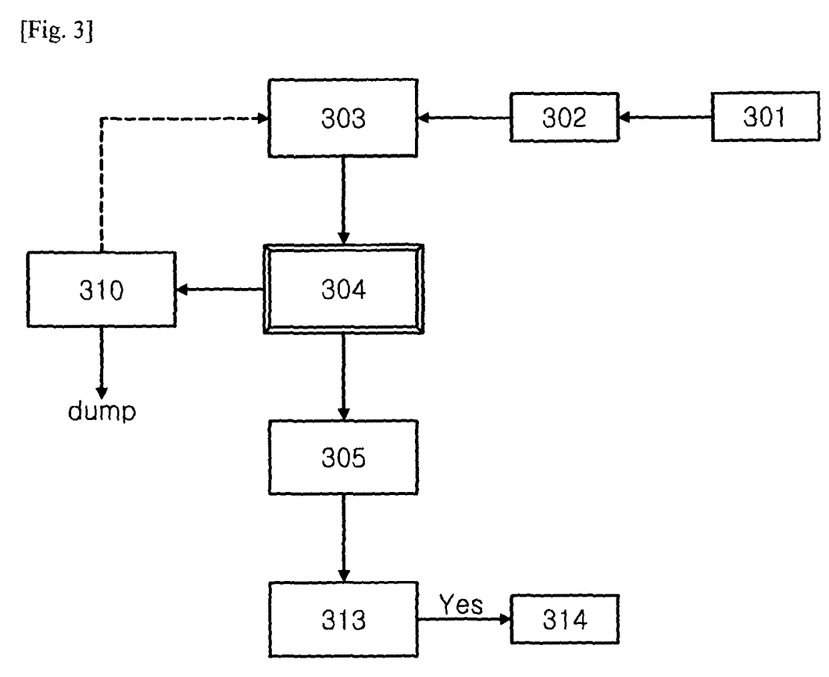
FIG. 3 is a block diagram schematically illustrating a separation process of a $^{17}O$ or $^{18}O$ isotope according to an embodiment of the present invention.

FIG. 1 is vapor pressure curves of formaldehyde, methanol, and water, FIG. 2 is a block diagram schematically illustrating a separation process of a $^{13}C$ isotope according to an embodiment of the present invention, and FIG. 3 is a block diagram schematically illustrating a separation process of a $^{17}O$ or $^{18}O$ isotope according to an embodiment of the present invention.

In the following descriptions, a "carbon isotope" is simply referred to as "$^{13}C$ isotope" and an "oxygen isotope" is referred to as "$^{17}O$ or $^{18}O$ isotope" if there is no specific description.

As shown in FIGS. 2 and 3, a separation of carbon and oxygen isotopes according to the embodiment of the present invention may be performed by separating formaldehyde vapor into hydrogen and carbon monoxide through photolysis.

A raw material used for the separation of carbon and oxygen isotopes is formaldehyde, in which formaldehyde in a vaporous state is supplied to photolysis reaction units 203 and 303. As shown in the vapor pressure curves of formaldehyde, methanol, and water in FIG. 1, a melting point of formaldehyde is −92° C. and a boiling point thereof is −21° C. Therefore, a photolysis reaction vessel may be maintained at a temperature in a range of 30° C. to 70° C. so as to contain formaldehyde in a molecular vapor form.

Photolysis processes 204 and 304 of formaldehyde may be performed by irradiating the formaldehyde vapor thus provided with light having a specific wavelength. In the present invention, an optical fiber laser is used for the photolysis of formaldehyde. The optical fiber laser refers to a laser having an active medium in an optical fiber, in which low levels of rare earth halides are added to the medium.

The optical fiber laser is small, lightweight, has ease of maintenance, and in particular, since the optical fiber laser has high energy efficiency and a wide irradiation wavelength range, the power thereof may be controlled within a wide range. Accordingly, a wavelength for the photolysis of formaldehyde may be selectively generated, and thus, the optical fiber laser may be suitable for being used in the present invention.

Among electronic transitions of formaldehyde, transitions of $v_2$, a C—O bond stretching mode, and $v_4$, an out-of-plane bending mode, are used as photolysis transition for the separation of carbon and oxygen isotopes.

A $2_0^04_0^1$ transition and a $2_0^04_0^3$ transition aimed at being used in the present invention are in a wavelength range of 340 nm to 360 nm. Therefore, when formaldehyde vapor having a pressure of a few Torr is irradiated with an ultraviolet light ray having a wavelength range of 340 nm to 360 nm, formaldehyde is photolyzed into hydrogen molecules and carbon monoxide, and quantum efficiency at this time is almost close to one.

In particular, when the foregoing optical fiber laser is used, a laser having a desired wavelength range may be irradiated, because the energy efficiency thereof is high, the maintenance thereof is facilitated, and the irradiation wavelength range thereof is wide. A laser having the foregoing wavelength range may be obtained through a $3^{rd}$ harmonic generation of the optical fiber laser.

When formaldehyde vapor is irradiated with an ultraviolet laser having the foregoing wavelength range, only formaldehyde including an isotope, such as $^{13}C$, $^{14}C$, $^{17}O$, or $^{18}O$, may be selectively photolyzed. A photoabsorption cross section of formaldehyde including an isotope, such as $^{13}C$, $^{14}$C, $^{17}$O, or $^{18}$O, at a formaldehyde transition wavelength used in a photolysis process is about $5 \times 10^{-20}$ cm$^2$/molecule at a pressure of a few Torr and a photoabsorption cross section of formaldehyde including a $^{12}$C or $^{16}$O isotope is about $2.5 \times 10^{-22}$ cm$^2$/molecule. Therefore, an isotope enrichment factor of the foregoing process is about 200 and thus, a high enrichment factor for photolysis may be obtained. For example, a laser having a wavelength of 352.53 nm, as an absorption wavelength of formaldehyde, may be selected and used in the case that $^{13}$C is aimed at being separated, and a laser having a wavelength of 352.20 nm may be used in the case that $^{14}$C is aimed at being separated, in which isotope enrichment factors ($\alpha$) of these two processes are about 200.

Figure 7:
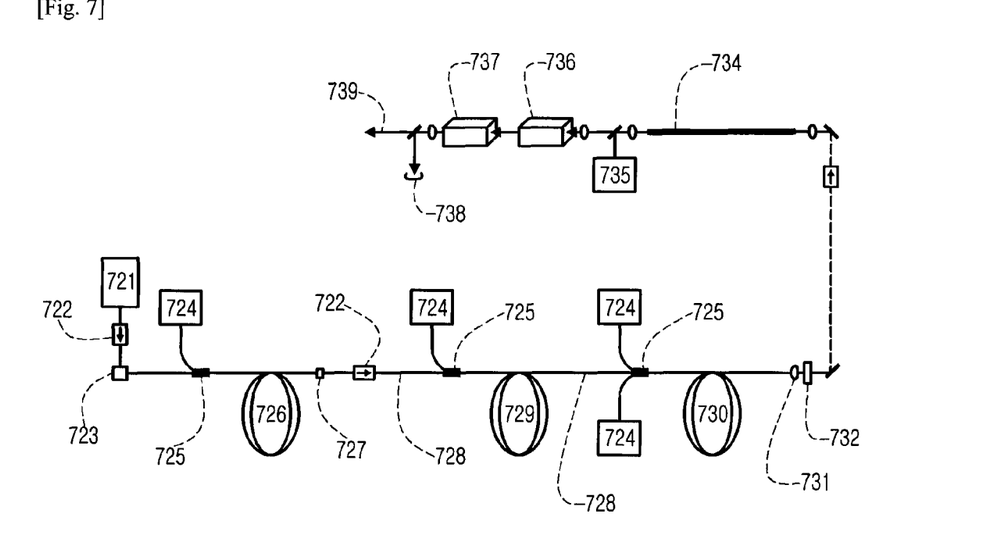
FIG. 7 is a schematic view illustrating a configuration of an optical fiber-based master-oscillator power-amplifier and a third harmonic generator for generating an ultraviolet light wavelength of 350 nm according to an embodiment of the present invention.

An example of an optical fiber laser apparatus used in the photolysis of formaldehyde into hydrogen and carbon monoxide is shown in FIG. 7. The optical fiber laser apparatus shown in FIG. 7 only illustrates an example of the optical fiber laser applicable to the present invention and the present invention is not limited thereto.

FIG. 7 is a schematic view illustrating an optical fiber-based master-oscillator power-amplifier and a third harmonic generator for generating ultraviolet light having a wavelength ranging from 340 nm to 360 nm.

A main configuration of the laser apparatus according to the present invention includes a main oscillator 721 irradiating a laser beam, an intensity modulator 723, a plurality of ytterbium-doped fiber amplifiers 726, 729 and 730 amplifying a laser power, and a second harmonic generator 736 and a third harmonic generator 737 converting a wavelength of the laser beam into an ultraviolet light wavelength ranging from 340 nm to 360 nm.

The main oscillator 721 may use a distributed feedback (DFB) diode laser. The DFB diode laser may have a wavelength ranging from 1020 nm to 1080 nm, operate in a continuous wave mode, and have a narrow width ranging from 1 MHz to 10 MHz and a power ranging from 10 mW to 100 mW.

The laser beam passes the intensity modulator 723 through an optical isolator 722 combined with an optical fiber and may be modulated to have a pulse repetition rate of a few hundred kHz and a pulse width ranging from 5 ns to 50 ns as the laser beam passes the intensity modulator 723. An acousto-optic modulator (AOM) may be used as the intensity modulator 723. The pulse modulated laser has a power ranging from 1 µW to 10 µW.

Accordingly, the pulse modulated laser may pass a pump laser diode 724 combined with an optical fiber, a pump, and a signal coupler 725. Further, the laser apparatus includes ytterbium-doped fibers acting as an amplifier in a wavelength range of 1020 nm to 1080 nm. The pulse modulated laser is amplified by the ytterbium-doped fibers, in which the pulse modulated laser having a power ranging from 1 µW to 10 µW may be amplified to have a power ranging from 1 W to 20 W as the laser passes through three-step ytterbium-doped fiber amplifiers 726, 729 and 730.

At this time, the ytterbium-doped fiber amplifiers 726, 729 and 730 may have a core having a diameter of 30 µm or less. Specifically, for example, the diameters of the cores of the ytterbium-doped fiber amplifiers 726, 729 and 730 may be about 6 µm, 10 µm, and 25 µm, respectively. Meanwhile, the laser passing through the ytterbium-doped fiber amplifier 726 may pass an optical filter 727 and an optical fiber mode field adapter 728 combined with optical fibers.

The laser amplified to a range of 1 W to 20 W by passing through the foregoing three-step ytterbium-doped fiber amplifiers 726, 729 and 730 passes through an optical lens 731, an optical filter 732, and an optical isolator 733, and then passes through a photonic crystal fiber amplifier 734 having a core diameter ranging from 50 MHz to 100 MHz. The laser may be amplified in a range of 200 W to 300 W by the photonic crystal fiber amplifier 734 and at this time, the width of the laser may be in a range of about 50 MHz to about 500 MHz.

The 200 W to 300 W infrared laser having a wavelength ranging from 1020 nm to 1080 nm is amplified through the foregoing optical fiber amplifiers 726, 729, 730, and 734, and passes the second harmonic generator 736, such as lithium triborate (LBO) photonic crystal, and the third harmonic generator 737, such as beta-barium borate photonic crystal to be converted into an ultraviolet (UV) laser beam 739 having a wavelength ranging from 340 nm to 360 nm. At this time, an average power of the laser beam may be about 100 W and the width of the laser beam may be in a range of about 150 MHz to about 1.5 GHz.

Fundamental and second harmonic beams are removed from the UV laser beam 739 thus obtained through a beam dump 738 and thus, the UV laser beam 739 having a wavelength range of 340 nm to 360 nm may be obtained. The UV laser beam 739 has a power of 100 W and a width of 1.5 GHz or less, sufficient for selectively photolyzing a large amount of formaldehyde including carbon and oxygen isotopes. Therefore, formaldehyde including $^{13}$C, $^{14}$C, $^{17}$O, or $^{18}$O may be selectively photolyzed into hydrogen and carbon monoxide when formaldehyde is irradiated with the UV laser beam 739.

Meanwhile, a few KW-class UV lasers may be obtained when a third harmonic is generated after amplifying the laser through parallel installation of the photonic crystal fiber amplifier 734.

Formaldehyde is irradiated with ultraviolet light having a wavelength range of 340 nm to 360 nm by using the foregoing optical fiber laser apparatus and thus, formaldehyde including carbon and oxygen isotopes may be selectively photolyzed.

Formaldehyde not photolyzed in the photolysis process is recovered in 210 and 310 and discharged, and, H$_2$ and CO, photolysis products obtained through photolysis are separated and recovered in 205 and 305. At this time, H$_2$ and CO, the photolysis products obtained through the photolysis, and remaining unphotolyzed formaldehyde may be recovered by cooling and condensation. As shown in FIG. 1, a freezing point of the unphotolyzed formaldehyde is −92° C. and the unphotolyzed formaldehyde may be condensed by cooling below the freezing point. However, since hydrogen and carbon monoxide still exist in a gaseous state even under a condensation condition of formaldehyde, hydrogen and carbon monoxide, photolysis reaction products, may be recovered in gaseous states and separated from formaldehyde.

At this time, since the discharged formaldehyde is formaldehyde not photolyzed in the photolysis process in which formaldehyde including carbon and oxygen isotopes may be included, the discharged formaldehyde may be recycled in 210 and 310 through the photolysis process of formaldehyde.

Since carbon and oxygen isotopes may be recovered by using the foregoing method and optical fiber laser and a $^{14}$C radioactive isotope may also be separated and removed by using the method, the method may be suitable for disposing nuclear carbon wastes.

That is, $^{17}$O, $^{15}$N, and $^{13}$C are included in materials used as coolants and as structural materials of a nuclear reactor, and these stable isotopes may generate $^{14}$C radioactive isotopes by reacting with reactor neutrons. Since $^{14}$C generated in the nuclear reactor is very harmful, there is a need for separating and safely storing $^{14}C$.

Therefore, a synthetic gas including carbon monoxide and hydrogen is generated from nuclear carbon including $^{14}C$ generated in a nuclear reactor by using a steam reforming process and formaldehyde is then synthesized. $^{14}C$ radioactive isotopes may be removed from the obtained formaldehyde through photolysis by using the foregoing UV laser and thus, an amount of treated radioactive waste may be decreased by separately capturing carbon monoxide including $^{14}C$ radioactive isotopes.

Figure 6:
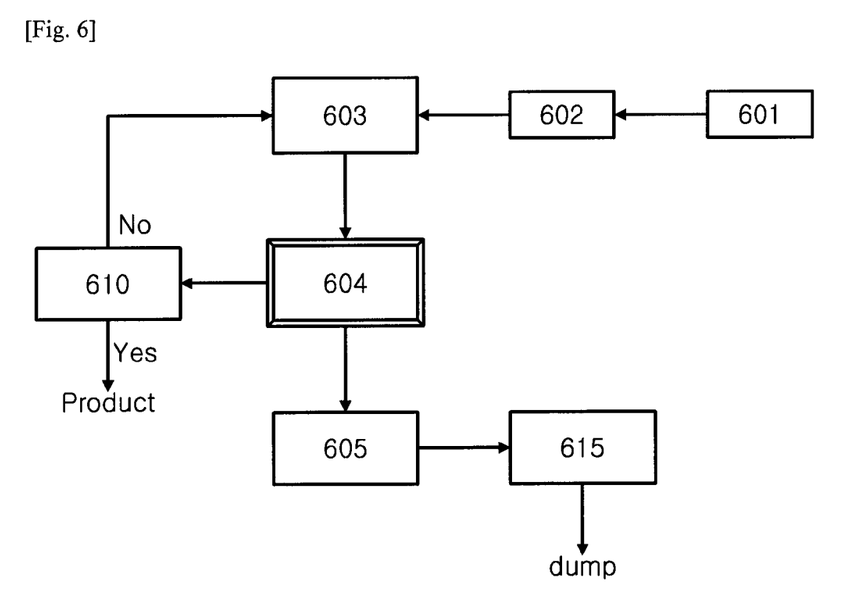
FIG. 6 is a block diagram schematically illustrating a process of removing a $^{14}C$ radioactive carbon isotope.

This is schematically shown in FIG. 6. However, detailed descriptions will not be provided here so as to avoid overlapping descriptions, and descriptions relating to the separation process of a carbon isotope will be substituted therefor.

In the case that a $^{14}C$ radioactive isotope is separated and removed by using the present invention, the $^{14}C$ radioactive isotope having a concentration of about 1 ppb may be decreased to have a concentration of about 5 ppt through a first-step process, and a $^{12}C$ isotope having a natural abundance ratio of 98.85% may be enriched to 99.9% or more by separating and removing a $^{13}C$ isotope having a natural abundance ratio of 1.11%.

Meanwhile, a targeted carbon isotope, $^{13}C$ or $^{14}C$, and a targeted oxygen isotope, $^{17}O$ or $^{18}O$, are included in the carbon monoxide generated through the foregoing photolysis of formaldehyde. Therefore, carbon and oxygen isotopes may be recovered from the residual photolysis product including carbon monoxide and hydrogen by catalytic oxidation reaction 211 and catalytic methanation reaction 313.

Specifically, hydrogen and carbon monoxide generated by the photolysis reaction 204 of formaldehyde are separated and recovered 205, and oxygen is then supplied to generate water ($H_2O$) and carbon dioxide ($CO_2$) by catalytic oxidation 211 and carbon dioxide is recovered by condensation of the water. Therefore, carbon dioxide having a carbon isotope enriched therein may be extracted as a final product 212. This may be expressed by the following Formula (1).

$$H_2+CO+O_2 \rightarrow CO_2+H_2O \quad (1)$$

Oxygen is supplied from the outside during the above process, but a degree of enrichment of carbon isotopes is not affected thereby.

A catalyst usable in the catalyst oxidation reaction 211 may be any catalyst typically used therein and is not particularly limited. For example, the catalyst may be Cu—Ce.

Meanwhile, in the case that the oxidation reaction used for separating a carbon isotope is used for a process of separating an oxygen isotope by using hydrogen and carbon monoxide generated through the photolysis reaction 304 of formaldehyde, changes in a degree of enrichment of oxygen isotope may be generated. Therefore, a method different from that used for the separation of a carbon isotope may be used.

In the present invention, after the separation and recovery 305 of hydrogen and carbon monoxide generated by the photolysis, the catalytic methanation reaction 313 may be performed in order to separate an oxygen isotope therefrom. Water and methane ($CH_4$) are generated from hydrogen and carbon monoxide by the catalytic methanation reaction 313 and water is recovered by condensation of the obtained water, and thus, water having an oxygen isotope enriched therein may be extracted as a final product 314. A reaction formula for the methanation reaction may be expressed by the following Formula (2).

$$3H_2+CO \rightarrow CH_4+H_2O \quad (2)$$

That is, water and methane may be obtained when hydrogen is supplied to hydrogen and carbon monoxide generated by the photolysis to generate the catalytic methanation reaction 313.

A catalyst usable in the catalyst methanation reaction 313 may be any catalyst typically used therein and is not particularly limited. For example, the catalyst may be Raney nickel.

Enrichment factors of carbon and oxygen isotopes in the photolysis process of formaldehyde (the first-step photolysis process) are in a range of about 100 to 200. Therefore, as another embodiment of the present invention, an additional separation process may be performed in order to obtain 95% or more of an isotope composition ratio from a carbon or oxygen isotope having a natural composition ratio.

Figure 4:
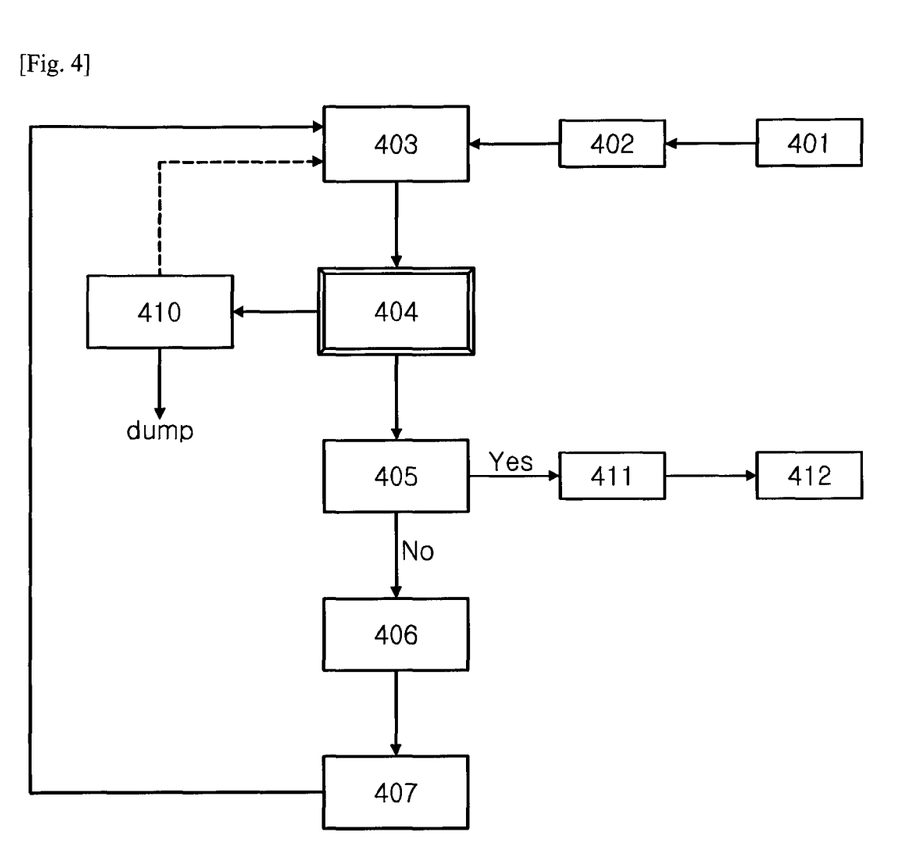
FIG. 4 is a block diagram schematically illustrating a separation process of a $^{13}C$ isotope according to an embodiment of the present invention, in which a second photolysis process is included.

This will be described in detail with reference to FIGS. 4 and 5. FIG. 4 is a block diagram schematically illustrating a second photolysis process for separating a carbon isotope according to an embodiment of the present invention, and FIG. 5 is a block diagram schematically illustrating a second-step photolysis process for separating an oxygen isotope according to an embodiment of the present invention.

Figure 5:
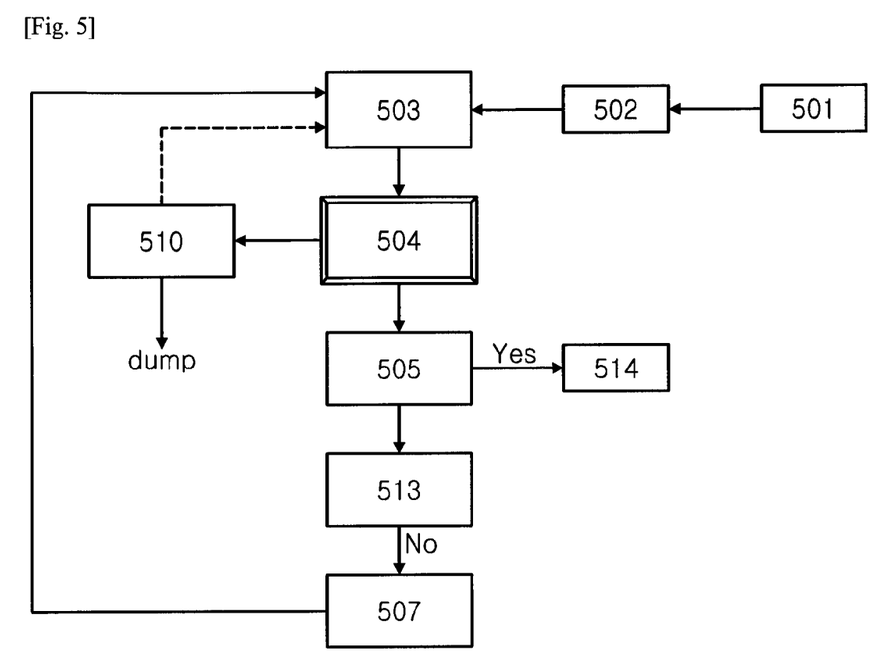
FIG. 5 is a block diagram schematically illustrating a separation process of a $^{17}O$ or $^{18}O$ isotope according to an embodiment of the present invention, in which a second photolysis process is included.

As shown in FIGS. 4 and 5, formaldehyde in a vaporous state is supplied from storage containers 402 and 502 storing a raw material, formaldehyde, to photolysis reaction units 403 and 503 and is photolyzed by using an optical fiber laser to obtain hydrogen and carbon monoxide 404 and 504. Processes for separating 410 and 510 formaldehyde not photolyzed by the photolysis reaction from the hydrogen and carbon monoxide to recover 405 and 505 hydrogen and carbon monoxide are the same as those of the embodiment described with reference to FIGS. 2 and 3 relating to the first-step separation process, and thus, detailed descriptions thereof will be omitted below. However, in FIGS. 4 and 5, reference numerals corresponding to those of FIGS. 2 and 3 indicate the same processes.

A second photolysis process by using an optical fiber laser must be undertaken in order to perform an additional separation process by using hydrogen and carbon monoxide generated in the first-step photolysis process, and for this purpose, there is a need for generating formaldehyde by using hydrogen and carbon monoxide, the photolysis products.

First, in the case that a carbon isotope is aimed at being separated, methanol is synthesized 406 from hydrogen and carbon monoxide generated through the first-step photolysis by a catalytic reaction and formaldehyde may be synthesized 407 from the synthesized methanol by a catalytic reaction. Reactions, in which methanol is synthesized 406 from hydrogen and carbon monoxide and formaldehyde is synthesized 407 from the synthesized methanol, may be expressed by the following Formulas (3) and (4).

$$2H_2+CO \rightarrow CH_3OH \quad (3)$$

$$2CH_3OH+O_2 \rightarrow 2CH_2O+2H_2O \quad (4)$$

A catalyst usable in the methanol synthesis reaction of Formula (3) is not particularly limited so long as the catalyst may be typically used therein. For example, CuB may be used. Further, a catalyst usable for synthesizing formaldehyde from methanol is not particularly limited so long as the catalyst may be typically used therein. For example, iron molybdate ($Fe_2O_3MoO_3$) may be used.

Formaldehyde synthesized by using the foregoing process is again supplied in a vaporous state to the second photolysis process 403 by an optical fiber laser to generate hydrogen and carbon monoxide 404 through photolysis of formaldehyde including a carbon isotope and unphotolized formaldehyde is extracted and recover 410, and thus, hydrogen and carbon monoxide may be separated 405.

Carbon dioxide including a carbon isotope and water are generated 411 from the obtained hydrogen and carbon monoxide including a carbon isotope through a catalytic oxidation reaction according to Formula (1) and carbon dioxide is recovered by condensation of water, and thus, a carbon isotope may be separated 412.

Meanwhile, in the case that an oxygen isotope is separated, water including an oxygen isotope is synthesized 513 from hydrogen and carbon monoxide generated from the first-step photolysis through a catalytic methanation reaction according to Formula (2), and separate formaldehyde not including an oxygen isotope is provided to the synthesized water to induce an oxygen-isotope exchange reaction between the synthesized water and the formaldehyde, and thus, formaldehyde including an oxygen isotope may be generated 507. The oxygen-isotope exchange reaction may be obtained by mixing water generated by the catalytic methanation reaction and formaldehyde, and may be expressed by the following Reaction (5).

$$CH_2{}^{16}O + H_2{}^{18}O \rightarrow CH_2{}^{18}O + H_2{}^{16}O \qquad (5)$$

An oxygen isotope included in the water enriched in the photolysis process may be transferred to formaldehyde by the oxygen-isotope exchange reaction and accordingly, formaldehyde including an oxygen isotope may be obtained. The obtained formaldehyde including an oxygen isotope is provided to the second photolysis process to be photolyzed and thus, separation 604 of oxygen isotope may be performed.

Also, methane and water including an oxygen isotope are generated through a catalytic methanation reaction according to Formula (2) and water is recovered by condensation of the generated water, and thus, an oxygen isotope may be separated.

The second separation process of carbon and oxygen isotopes is undertaken according to the foregoing method and thus, the enrichment factors of carbon and oxygen isotopes may be improved to a range of about 20,000 to about 40,000. These enrichment factors are sufficient for obtaining about 95% or more of the degrees of enrichment of carbon and oxygen isotopes from carbon and oxygen isotopes having natural composition ratios.

Carbon and oxygen isotope separation apparatuses suitable for the photolysis process according to the embodiment of the present invention will be described with reference to FIGS. 8 and 9. The isotope separation apparatuses described below and shown in FIGS. 8 and 9 are only examples of the present invention and are not limited by the descriptions below.

Figure 8:
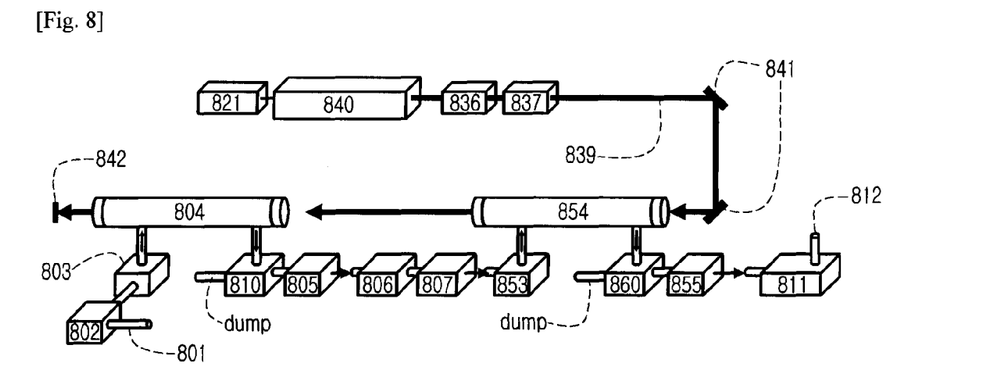
FIG. 8 is a schematic view illustrating a second separation apparatus for separating a carbon isotope according to an embodiment of the present invention.

FIG. 8 illustrates a second separation apparatus for separating a carbon isotope according to the present invention. Referring to FIG. 8, the isotope separation apparatus includes a first-step formaldehyde vapor supply unit 803; a first-step formaldehyde photolysis reaction unit 804; a formaldehyde recovery unit 810 recovering formaldehyde not photolyzed in the first step; an output unit 805 for hydrogen and carbon monoxide, first-step photolysis products; a methanol synthesis unit 806 synthesizing methanol from the first-step photolysis products, hydrogen and carbon monoxide; a formaldehyde synthesis unit 807 synthesizing formaldehyde from methanol, a first-step product; a formaldehyde vapor supply unit 853 supplying formaldehyde vapor to a second step; a second formaldehyde photolysis reaction unit 854; a formaldehyde recovery unit 860 recovering formaldehyde not photolyzed in the second step; an output unit 855 for hydrogen and carbon monoxide, second photolysis products; a catalytic oxidation reaction unit 811 for hydrogen and carbon monoxide for extracting an enriched carbon isotope; a carbon dioxide product 812 having a carbon isotope enriched therein; a main oscillator 821 using a DFB diode laser; an optical fiber amplifier 840; a second harmonic generator 836; and a third harmonic generator 837, and accordingly, an ultraviolet laser beam 839 having a wavelength range of 340 nm to 360 nm is generated. 45 degree UV reflection mirrors 841 and an UV retroreflection mirror 842 may be included for the transferral and effective use of the obtained UV laser beam, if necessary.

Figure 9:
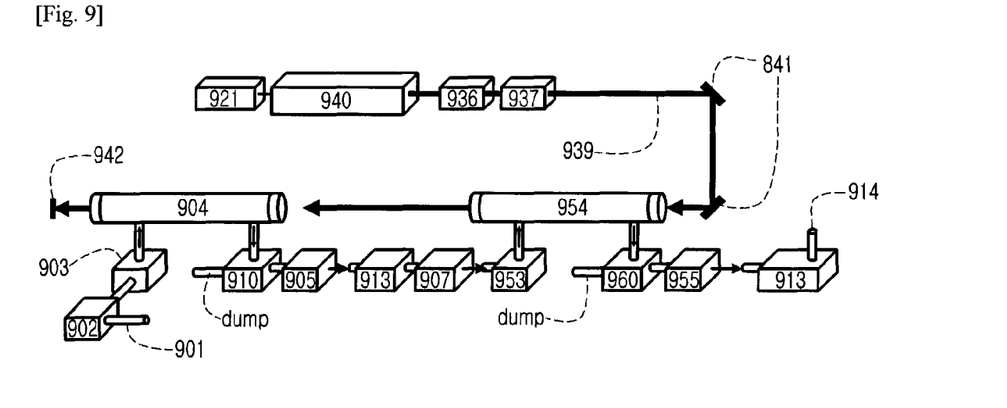
FIG. 9 is a schematic view illustrating a second separation apparatus for separating an oxygen isotope according to an embodiment of the present invention.

FIG. 9 illustrates a second separation apparatus for separating an oxygen isotope according to the present invention. Referring to FIG. 9, the isotope separation apparatus of the present invention includes a first-step formaldehyde vapor supply unit 903; a first-step formaldehyde photolysis reaction unit 904; a formaldehyde recovery unit 910 recovering formaldehyde not photolyzed in the first step; an output unit 905 for hydrogen and carbon monoxide, first-step photolysis products; a catalytic methanation reaction unit 913 for synthesizing water from the first-step photolysis products, hydrogen and carbon monoxide; an oxygen-isotope exchange reaction unit 907 for formaldehyde and water, a first-step product; a formaldehyde vapor supply unit 953 supplying formaldehyde vapor to a second step; a second formaldehyde photolysis reaction unit 954; a formaldehyde recovery unit 960 recovering formaldehyde not photolyzed in the second step; an output unit 955 for hydrogen and carbon monoxide, second photolysis products; the catalytic methanation reaction unit 913 for hydrogen and carbon monoxide for extracting an enriched oxygen isotope; a water product 914 having an oxygen isotope enriched therein; a main oscillator 921 using a DFB diode laser; an optical fiber amplifier 940; a second harmonic generator 936; and a third harmonic generator 937, and accordingly, an ultraviolet laser beam 939 having a wavelength range of 340 nm to 360 nm is generated. 45 degree UV reflection mirrors 941 and an UV retroreflection mirror 942 may be included for the transferral and effective use of the obtained UV laser beam, if necessary.

Referring to FIGS. 8 and 9, the carbon and oxygen isotope separation apparatuses using an optical fiber laser according to the present invention and separation processes will be described.

Formaldehyde, a raw material used for the separation of carbon and oxygen isotopes, is supplied 801 and 901 from formaldehyde containers 802 and 902 to the fist-step formaldehyde vapor supply units 803 and 903. In the first-step formaldehyde vapor supply units 803 and 903, formaldehyde in a vaporous state is supplied to the first-step photolysis reaction units 804 and 904 by using the vapor pressure curve shown in FIG. 1. Reaction vessels of the first-step photolysis reaction units 804 and 904 may be maintained at temperatures in a range of about 30° C. to about 70° C. so as to allow formaldehyde to be in a molecular vapor form.

The formaldehyde vapor thus supplied is irradiated with a light having a wavelength ranging from 340 nm to 360 nm by using the optical fiber laser as shown in FIG. 6 and thus, formaldehyde may be photolyzed.

Laser beams having a wavelength range of 1020 nm to 1080 nm emitted from the main oscillators 821 and 921 using DFB diode lasers are converted into ultraviolet light having a wavelength ranging from 340 nm to 360 nm through the optical fiber amplifiers 840 and 940. According to the optical fiber amplifiers 840 and 940, the laser beam may be converted into ultraviolet light having a specific wavelength through the following process, as shown in FIG. 7.

Laser beams having a wavelength range of 1020 nm to 1080 nm emitted from the main oscillators 721, 821, and 921 using DFB diode lasers have a width ranging from 1 MHz to 10 MHz and a power ranging from 10 mW to 100 mW, and are modulated into pulses having a pulse repetition rate of a few hundred kHz and a pulse width ranging from 5 ns to 50 ns as passing the intensity modulator 723. An acousto-optic modulator (AOM) may be used as the intensity modulator 723. Accordingly, the pulse modulated laser may have an average power ranging from 1 µW to 10 µW.

The pulse modulated laser passes the ytterbium-doped fibers acting as an amplifier in a wavelength range of 1020 nm to 1080 nm. The pulse modulated laser having an average power ranging from 1 µW to 10 µW is amplified to have a power ranging from 1 W to 20 W as the laser passes the three-step ytterbium-doped fiber amplifiers 726, 729 and 730, and may be again amplified in a range of 200 W to 300 W by the photonic crystal fiber amplifier 734 having a core diameter ranging from 50 µm to 100 µm. At this time, the width of the laser may be in a range of about 50 MHz to about 500 MHz.

The few hundred W-class infrared lasers having a wavelength ranging from 1020 nm to 1080 nm are converted into ultraviolet laser beams 739, 839, and 939 having a wavelength ranging from 340 nm to 360 nm while passing the second harmonic generators 736, 836, and 936, and the third harmonic generators 737, 837, and 937. At this time, an average power of the laser beams may be about 100 W and the width of the laser beams 739, 839, and 939 may be in a range of about 150 MHz to about 1.5 GHz.

The ultraviolet laser beams 739, 839, and 939 thus obtained may have powers and widths sufficient for selectively photolyzing a large amount of formaldehyde including carbon and oxygen isotopes. Therefore, formaldehyde including $^{13}C$, $^{14}C$, $^{17}O$, or $^{18}O$ may be selectively photolyzed into hydrogen and carbon monoxide when formaldehyde is irradiated with the ultraviolet laser beams.

Meanwhile, a few kW-class UV laser beams may be obtained when a third harmonic is generated after amplifying the laser through parallel installation of the photonic crystal fiber amplifier 734.

Photolysis reaction units 804 and 904 are irradiated with ultraviolet light having a wavelength range of 340 nm to 360 nm by using the foregoing laser apparatuses and thus, formaldehyde including carbon and oxygen isotopes, such as $^{13}C$, $^{14}C$, $^{17}O$, or $^{18}O$, may be selectively photolyzed to generate hydrogen and carbon monoxide.

Formaldehyde not photolyzed by the photolysis reaction is discharged to the formaldehyde recovery units 810 and 910, and accordingly, hydrogen and carbon monoxide, photolysis products, may be recovered 805 and 905. At this time, the unphotolyzed formaldehyde is cooled and condensed to be discharged to the formaldehyde recovery units 810 and 910, and thus, the photolysis products, hydrogen and carbon monoxide, may be separated and recovered 805 and 905.

At this time, since the discharged unphotolyzed formaldehyde may include formaldehyde including a carbon or oxygen isotope, the discharged unphotolyzed formaldehyde may be reintroduced into the photolysis reaction units 804 and 904 by recycling through any one of the first-step formaldehyde supply units 801 and 901, the formaldehyde storage containers 802 and 902, or the formaldehyde vapor supply units 803 and 903.

Meanwhile, since a targeted carbon isotope, $^{13}C$ or $^{14}C$, and a targeted oxygen isotope, $^{17}O$ or $^{18}O$, are included in the carbon monoxide generated through the foregoing photolysis of formaldehyde, a carbon isotope or oxygen isotope may be recovered by a catalytic oxidation reaction or catalytic methanation reaction after the photolysis product is supplied to the catalytic oxidation reaction unit 811 or the catalytic methanation reaction unit 913. The recovery of carbon and oxygen isotopes by the catalytic oxidation and catalytic methanation reactions will be described in detail below.

Enrichment factors of carbon and oxygen isotopes in the photolysis process of formaldehyde (the first-step photolysis process) are in a range of about 100 to 200. Therefore, a second separation process may be performed in order to obtain 95% or more of an isotope composition ratio from a carbon isotope or oxygen isotope having a natural composition ratio.

First, in order to separate a carbon isotope, hydrogen and carbon monoxide generated by the first-step photolysis are supplied from the hydrogen and carbon monoxide output unit 805 to the methanol synthesis unit 806 to generate methanol by a catalytic reaction according to Formula (3). The synthesized methanol is provided to the formaldehyde synthesis unit 807 and oxygen is supplied to the formaldehyde synthesis unit 807, and thus, formaldehyde may be synthesized by a catalytic reaction according to Formula (4).

Meanwhile, in order to separate an oxygen isotope, hydrogen and carbon monoxide generated by the first-step photolysis are supplied from the hydrogen and carbon monoxide output unit 905 to the methanation reaction unit 913 to generate water and methane by a catalytic methanation reaction according to Formula (2). The synthesized water is provided to the oxygen-isotope exchange reaction unit 907 and formaldehyde is supplied thereto, and thus, formaldehyde including an oxygen isotope may be generated by inducing an oxygen-isotope exchange reaction according to Formula (5).

The formaldehyde including a carbon or oxygen isotope synthesized according to the foregoing processes passes the second formaldehyde vapor supply units 853 and 953 to be converted into formaldehyde in a vaporous state, and the formaldehyde in a vaporous state is supplied to the second photolysis reaction units 854 and 954 to generate hydrogen and carbon monoxide by photolysis of the formaldehyde vapor.

The second photolysis reaction units 854 and 954 having the obtained formaldehyde supplied thereto are irradiated with ultraviolet laser beams 739, 839, and 939 having a wavelength ranging from 340 nm to 360 nm generated by the optical fiber laser apparatus according to FIG. 7 to photolyze the formaldehyde into hydrogen and carbon monoxide. At this time, the photolysis reaction is the same as that of the first-step photolysis reaction unit.

Unphotolyzed formaldehyde is removed from hydrogen and carbon monoxide, the photolysis products thus generated, through the unphotolyzed formaldehyde recovery units

860 and 960, and hydrogen and carbon monoxide are output to the hydrogen and carbon monoxide output units 855 and 955 and recovered.

Water and carbon dioxide are generated from the hydrogen and carbon monoxide generated through the photolysis by a catalytic oxidation reaction according to Formula (1) in the catalytic oxidation reaction unit 811, and carbon dioxide in a gaseous state is then recovered by condensation of the water. Therefore, carbon dioxide having a carbon isotope enriched therein may be extracted as the final product 812.

Meanwhile, hydrogen and carbon monoxide, the photolysis products for the photolysis of an oxygen isotope, are provided to the catalytic methanation reaction unit 913 to generate water and methane according to Formula (2) and the obtained water is condensed and recovered. Therefore, water having an oxygen isotope enriched therein may be extracted as the final product 914.

Formaldehyde is photolyzed by methods and apparatuses according to the embodiments of the present invention and thus, $^{18}$O-enriched water having 95% of $^{18}$O and $^{13}$C-enriched carbon dioxide ($^{13}$CO$_2$) having 99% of $^{13}$C may be produced.

Also, annual facility production may be innovatively increased and a facility start-up time may be decreased by using a third harmonic due to an optical fiber laser according to the embodiment of the present invention.

Meanwhile, an optical fiber laser having high energy efficiency and easy maintenance features is used in the recovery of carbon and oxygen isotopes, and thus, it is commercially useful for separating carbon and oxygen isotopes as well as economical because carbon and oxygen isotopes may be separated and produced by using a small-scale facility.

Further, the disposal of nuclear carbon wastes, such as nuclear graphite, may be effectively performed, as effective separation and removal of a $^{14}$C radioactive isotope may be possible by using small-scale facility and apparatus.

While the present invention has been shown and described in connection with the exemplary embodiments, it will be apparent to those skilled in the art that modifications and variations can be made without departing from the spirit and scope of the invention as defined by the appended claims.

The invention claimed is:

1. A method of separating a carbon isotope, the method comprising:
    performing a first photolysis process on formaldehyde, including a carbon isotope, by irradiation thereof with ultraviolet light having a wavelength ranging from 340 nm to 360 nm to generate carbon monoxide having a carbon isotope enriched therein and hydrogen;
    extracting and removing unphotolized formaldehyde and recovering the carbon monoxide having a carbon isotope enriched therein and hydrogen;
    performing formaldehyde synthesis for synthesizing formaldehyde having a carbon isotope enriched therein by using the recovered carbon monoxide having a carbon isotope enriched therein and hydrogen, wherein methanol is synthesized from the hydrogen and the carbon monoxide having a carbon isotope enriched therein by a catalytic reaction, and the formaldehyde having a carbon isotope enriched therein is synthesized from the synthesized methanol by a catalytic reaction;
    performing a second photolysis process for generating carbon monoxide having a carbon isotope enriched therein and hydrogen through photolysis by irradiating the synthesized formaldehyde having a carbon isotope enriched therein with ultraviolet light having a wavelength range of 340 nm to 360 nm;
    performing a catalytic oxidation reaction on the carbon monoxide having a carbon isotope enriched therein and the hydrogen generated by the second photolysis process to synthesize carbon dioxide (CO$_2$) having a carbon isotope enriched therein and water (H$_2$O); and
    cooling the H$_2$O to recover CO$_2$ having a carbon isotope enriched therein.

2. The method of claim 1, wherein the photolysis is performed by irradiation with a third harmonic generated by an optical fiber laser.

3. The method of claim 1, wherein, after infrared light having a wavelength ranging from 1020 nm to 1080 nm is pulse modulated and amplified by an optical fiber amplifier, ultraviolet light having a wavelength ranging from 340 nm to 360 nm is formed by converting the infrared light into a third harmonic.

4. A method of separating an oxygen isotope, the method comprising:
    performing a first photolysis process on formaldehyde including an oxygen isotope by irradiation with ultraviolet light having a wavelength ranging from 340 nm to 360 nm to generate carbon monoxide having an oxygen isotope enriched therein and hydrogen;
    extracting and removing unphotolized formaldehyde and recovering the carbon monoxide having an oxygen isotope enriched therein and hydrogen;
    performing formaldehyde generation for generating formaldehyde having an oxygen isotope enriched therein by using the recovered carbon monoxide having an oxygen isotope enriched therein and hydrogen, wherein methane and water are synthesized from the hydrogen and the carbon monoxide having an oxygen isotope enriched therein by a catalytic methanation reaction, and the formaldehyde having an oxygen isotope enriched therein is generated by mixing the synthesized water with formaldehyde to generate an oxygen-isotope exchange reaction between the water and the formaldehyde;
    performing a second photolysis process for generating carbon monoxide having an oxygen isotope enriched therein and hydrogen through photolysis by irradiating the synthesized formaldehyde having an oxygen isotope enriched therein with ultraviolet light having a wavelength range of 340 nm to 360 nm;
    performing a catalytic methanation reaction on the carbon monoxide having an oxygen isotope enriched therein and the hydrogen generated by the second photolysis process to synthesize water (H$_2$O) and methane (CH$_4$); and
    cooling the H$_2$O to recover H$_2$O having an oxygen isotope enriched therein.

5. The method of claim 4, wherein the photolysis is performed by irradiation with a third harmonic generated by an optical fiber laser.

6. The method of claim 4, wherein, after infrared light having a wavelength ranging from 1020 nm to 1080 nm is pulse modulated and amplified by an optical fiber amplifier, the ultraviolet light having a wavelength ranging from 340 nm to 360 nm is formed by converting the infrared light into a third harmonic.

7. The method of claim 1, wherein the ultraviolet light having a wavelength ranging from 340 nm to 360 nm is generated by an optical fiber laser apparatus comprising:
    a main oscillator irradiating a laser having a wavelength range of 1020 nm to 1080 nm;

an intensity modulator modulating a pulse of the laser;
a plurality of ytterbium-doped fiber amplifiers amplifying a power of the pulse modulated laser; and
second and third harmonic generators converting a wavelength of the power amplified laser into an ultraviolet light wavelength ranging from 340 nm to 360 nm.

8. The method of claim 4, wherein the ultraviolet light having a wavelength ranging from 340 nm to 360 nm is generated by an optical fiber laser apparatus comprising:
a main oscillator irradiating a laser having a wavelength range of 1020 nm to 1080 nm;
an intensity modulator modulating a pulse of the laser;
a plurality of ytterbium-doped fiber amplifiers amplifying a power of the pulse modulated laser; and
second and third harmonic generators converting a wavelength of the power amplified laser into an ultraviolet light wavelength ranging from 340 nm to 360 nm.

\* \* \* \* \*